(12) United States Patent
Kim et al.

(10) Patent No.: US 11,783,518 B2
(45) Date of Patent: Oct. 10, 2023

(54) FEW-VIEW COMPUTED TOMOGRAPHY RECONSTRUCTION USING DEEP NEURAL NETWORK INFERENCE

(71) Applicant: Lawrence Livermore National Security, LLC, Livermore, CA (US)

(72) Inventors: Hyojin Kim, Davis, CA (US); Rushil Anirudh, Dublin, CA (US); Kyle Champley, Pleasanton, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 204 days.

(21) Appl. No.: 17/038,565

(22) Filed: Sep. 30, 2020

(65) Prior Publication Data

US 2021/0097737 A1    Apr. 1, 2021

Related U.S. Application Data

(60) Provisional application No. 62/907,841, filed on Sep. 30, 2019.

(51) Int. Cl.
| | |
|---|---|
| *G06T 11/00* | (2006.01) |
| *G06T 9/00* | (2006.01) |
| *G06N 3/088* | (2023.01) |
| *G06N 3/045* | (2023.01) |
| *A61B 6/03* | (2006.01) |

(52) U.S. Cl.
CPC ............ *G06T 11/006* (2013.01); *G06N 3/045* (2023.01); *G06N 3/088* (2013.01); *G06T 9/002* (2013.01); *A61B 6/032* (2013.01)

(58) Field of Classification Search
CPC ......... G06T 11/006; G06T 9/002; G06T 9/00; G06T 11/00; G06N 3/08; G06N 3/04; G06N 3/088; G06N 3/0454
See application file for complete search history.

(56) References Cited

U.S. PATENT DOCUMENTS

2019/0380670 A1* 12/2019 Hofmann ............... G06T 11/008
2021/0035338 A1*  2/2021 Zhou ....................... G06N 20/20

OTHER PUBLICATIONS

Anirudh, R. et al. "Lose the views: Limited angle CT reconstruction via implicit sinogram completion." In 2018 IEEE/CVF Conference on Computer Vision and Pattern Recognition, pp. 6343-6350, 2018.
Champley, K.M. "Livermore tomography tools (LTT) technical manual." Tech. Rep. LLNL-SM-687016, LLNL, Livermore, CA, USA, 2016.

(Continued)

*Primary Examiner* — Tuan H Nguyen
(74) *Attorney, Agent, or Firm* — Perkins Coie LLP (57) ABSTRACT

A system for generating 2D slices of a 3D image of a target volume is provided. The system receives a target sinogram collected during a computed tomography scan of the target volume. The system inputs the target sinogram to a convolutional neural network (CNN) to generate predicted 2D slices of the 3D image. The CNN is trained using training 2D slices of training 3D images. The system initializes 2D slices to the predicted 2D slices. The system reconstructs 2D slices of the 3D image from the target sinogram and the initialized 2D slices.

15 Claims, 4 Drawing Sheets

(56) References Cited

OTHER PUBLICATIONS

Chen, H. et al. "Low-dose CT with a residual encoderdecoder convolutional neural network." IEEE Transactions on Medical Imaging, 36(12):2524-2530, 2017.

Fessler, Jeffrey A. et al. "Conjugate-gradient preconditioning methods for shift-variant pet image reconstruction," IEEE Trans. Imag. Proc., 8:688-699, 1999.

Gupta, H. et al. "Cnn-based projected gradient descent for consistent CT image reconstruction." IEEE Transactions on Medical Imaging, 37(6):1440-1453, 2018.

He, K. et al., "Deep Residual Learning for Image Recognition," in Proceedings of the IEEE conference on computer vision and pattern recognition, 2016, pp. 770-778.

Herman, G.T. et al. "Image reconstruction from a small number of projections," Inverse Problems 24(4), 2008.

Jin, K.H. et al. "Deep convolutional neural network for inverse problems in imaging." IEEE Transactions on Image Processing, 26(9):4509-4522, 2017.

Kak, A.C. et al. "Principles of Computerized Tomographic Imaging." Society of Industrial and Applied Mathematics, 2001.

National Cancer Institute. Data Science Bowl 2017—"Chest CT dataset for lung nodule detection." 2017. <www.kaggle.com/c/data-science-bowl-2017/overview/description>.

Ritschl, L. et al. "Improved total variation-based CT image reconstruction applied to clinical data." Physics in Medicine and Biology, 56(6):1545-1561, 2011.

Sidky, E.Y. et al. "Image reconstruction in circular cone-beam computed tomography by constrained, total-variation minimization." Phys. Med. Biol., 53:4777-4807, 2008.

Wang, Z. et al. "Image quality assessment: from error visibility to structural similarity." IEEE Trans. Imag. Proc., 13(4):600-612, 2004.

Xu, Q. et al. "Low-dose x-ray CT reconstruction via dictionary learning." IEEE Transactions on Medical Imaging, 31(9):1682-1697, 2012.

Ye, D.H. et al. "Deep back projection for sparse-view CT reconstruction." IEEE Global Conference on Signal and Information Processing (GlobalSIP), pp. 1-5, 2018.

\* cited by examiner

FIG. 4

FEW-VIEW COMPUTED TOMOGRAPHY RECONSTRUCTION USING DEEP NEURAL NETWORK INFERENCE

CROSS-REFERENCE TO RELATED APPLICATION(S)

This application claims the benefit of priority to U.S. Provisional Patent Application No. 62/907,841 filed on Sep. 30, 2019, which is hereby incorporated by reference in its entirety.

STATEMENT REGARDING FEDERALLY SPONSORED RESEARCH

The United States government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND

In many environments, there is a need to identify regions of interest within an image. For example, in an airport, an image generated from a scan of a bag may need to be analyzed to determine whether the bag contains any prohibited objects. As another example, for clinical diagnosis, an image generated from a scan of a patient may need to be analyzed to determine whether the patient has a tumor. The scanning technology may be computed tomography ("CT"), and the images may be three-dimensional ("3D") images.

CT is a technique that noninvasively generates cross-sectional images (or views) of the linear attenuation coefficients ("LACs") of materials in an object of interest (target volume). CT has been used extensively in medical and security applications such as for generating a scan of a brain or a scan of baggage at an airport. The LAC is a measure of the attenuation of X-rays as the X-rays pass through a certain material and is in units of inverse length (e.g., per centimeter). To generate the LACs, CT employs an X-ray source and an X-ray detector. The X-ray source transmits X-rays through the object with an initial intensity, and the X-ray detector, which is on the opposite side of the object from the source, measures the final intensities of the X-rays that pass through the object and impinge on pixels of a detector. CT collects measurements by positioning the source and detector at various angles relative to the object and collects the measurements of the final intensity at each angle. The measurements for an angle are referred to as a projection or a view. The measurements of the intensities may be represented as a negative of a logarithm of a ratio of transmission data of a scan of the object to transmission data of a scan without the object (e.g., scan of air). Various techniques may be used to collect measurements at different angles relative to the object. For example, the source and detector may be stationary and the object may be rotated, the object may be stationary and the source and detector may be rotated, and multiple stationary transmitters and detectors may be positioned at different angles. CT algorithms then reconstruct from the collection of measurements a 3D image of the object that specifies the LAC for each volume element ("voxel") with the volume of the object. The cross-sectional images are generated from the 3D image.

Conventional CT generally require that the number of projections be roughly equal to the number of pixels in a projection depending on scanner resolution and the view row size. In practice, the number of projections that can be collected may be severely limited for various reasons. For example, some CT protocols require that the X-ray dose delivered to the object (e.g., baggage or patient) be limited. One way to reduce the dose is to limit the number of projections that are collected. As another example, CT systems that are flux-limited may employ long integration times per projection to collect adequate measurements. CT systems may be flux-limited because of dim sources (low current), large source-to-detector distances, small detector pixels, and/or highly attenuating objects. To increase throughput, a flux-limited CT system may have time to generate only a small number of projections. As another example, when the object is in motion (e.g., a beating human heart), a CT system may deliberately collect a limited number of projections to shorten the data acquisition time to reduce the artifacts associated with the object motion. As another example, some CT systems employ multiple source-detector pairs mounted on a stationary gantry (e.g., for scanning carry-on baggage at an airport). The projections of such a CT system are limited by the number of sources.

When the number of projections is limited to one or more orders of magnitude smaller than the number pixels in a projection, a problem arises in that the reconstructed 3D image is generally polluted with streak artifacts. This problem is referred to as a limited-view (e.g., in the range of 100-200 views) or a few-view (e.g., in the range of 20 or less views) reconstruction problem. The reconstruction problem arises because the number of unknowns (i.e., the number of voxels) is much greater than the number of linear equations represented by the projections and the measurements are noisy.

DETAILED DESCRIPTION

A method and system are provided for image reconstruction using a convolutional neural network (CNN) inference-based reconstruction algorithm to address extremely few-view CT imaging scenarios. In some embodiments, a CNN inference reconstruction ("CNNIR") system enables recovery of perceptual information as well as contextual features from the small number of X-ray projections or views (i.e., a sinogram). In order to ensure that the reconstructed image is consistent with an input sinogram (and in order not to contain perceptually created but incorrect regions in the reconstructed images), the CNNIR system employs predicted 2D slices of a 3D image or a predicted 3D image of a target object or volume as priors in the iterative algorithm for final reconstruction of final 2D slices of the 3D image or the final 3D image.

In some embodiments, the CNNIR system receives a target sinogram collected during a computed tomography scan of a target volume. For example, the scan may be of the chest of a patient. Each target view of the target sinogram may be collected by an X-ray detector that detects X-rays (or more generally electromagnetic rays) transmitted by an X-ray scanner through the target volume. Each target view is collected from a different angle. For example, the target sinogram may a few-view sinogram with target views collected an at five angles between 0 and 90 degrees. The CNNIR system inputs the target sinogram to a CNN to generate predicted 2D slices of the 3D image. The CNNIR system trains the CNN using training 2D slices of training 3D images. The CNNIR initializes 2D slices of the reconstruction algorithm to the predicted 2D slices. The CNNIR system then reconstructs final 2D slices of the 3D image from the target sinogram and the initialized 2D slices. Because the reconstruction algorithm is initialized to the predicted 2D slices, the final 2D slices are a more accurate reconstruction of the 3D image than when a standard initialization technique is used such as setting the initial 2D slices to all zeros.

Although described primarily in the context of predicting 2D slices for initializing 2D slices for a reconstruction, the CNNIR system may be employed to predict a 3D image for initializing a 3D image for reconstruction. The predicting of a 3D image may be employed for reconstructing 3D images based on sinograms collected using cone-beam or helical scanners. So, more generally, the CNNIR system generates a 3D representation of a 3D image (e.g., 2D slices or a 3D image) of a target volume from target views representing a scan of the target volume. The CNNIR system generates an initial 3D representation by inputting the target views to a convolutional neural network (CNN) that is trained to generate a 3D representation from the target views. The CNNIR system then reconstructs the 3D representation from the target views and the initial 3D representation.

Figure 1:
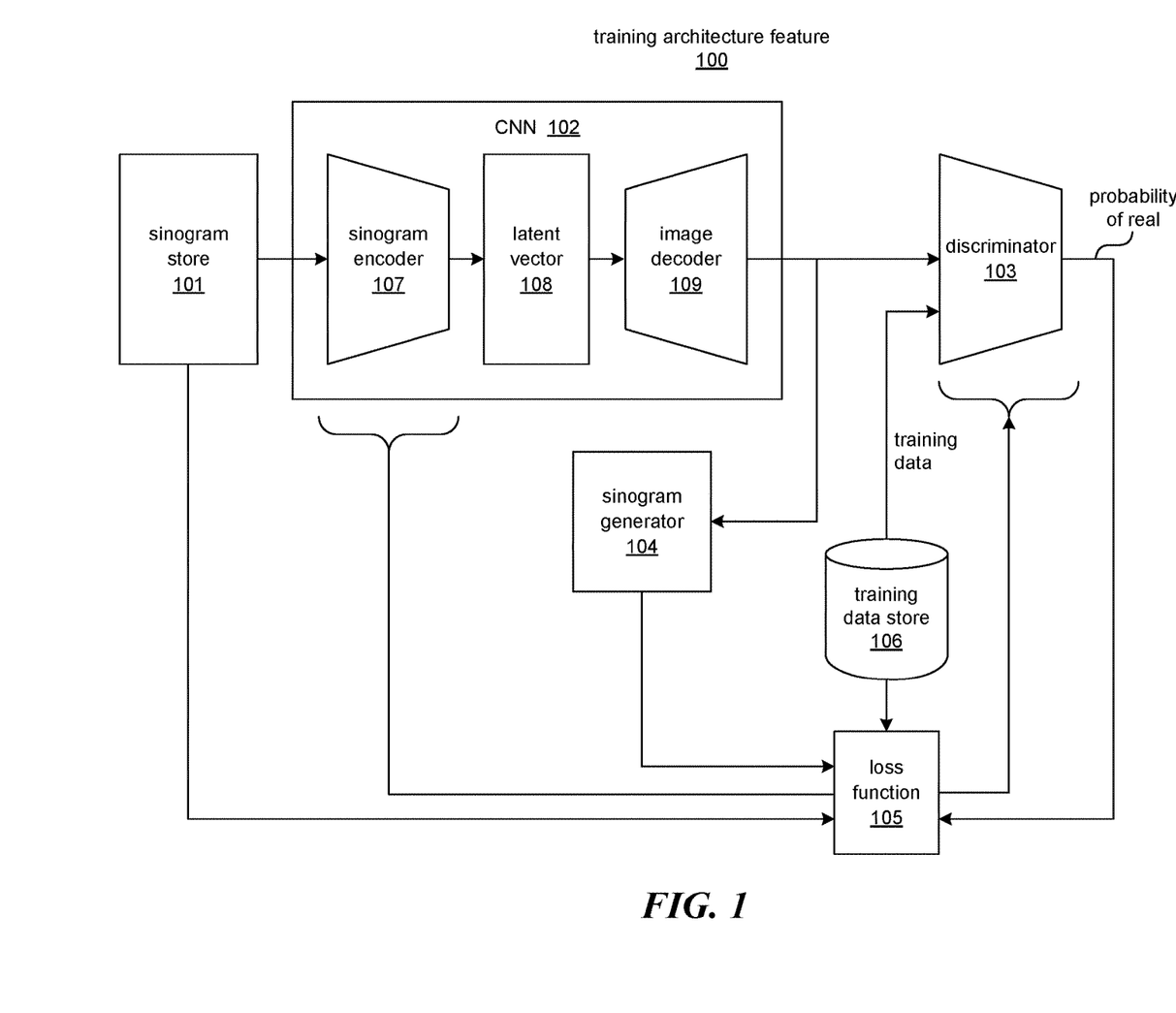
FIG. 1 is a block diagram that illustrates a training architecture used in training the CNN in some embodiments.

FIG. 1 is a block diagram that illustrates a training architecture used in training the CNN in some embodiments. In some embodiments, the training architecture 100 includes a sinogram store 101, a CNN 102, a discriminator 103, a sinogram generator 104, a loss function 105, and a training data store 106. The CNN includes an encoder 107 (a 1D CNN) that inputs a sinogram and outputs a latent vector 108 representing the sinogram and an image decoder 109 (a 2D CNN) that inputs the latent vector and outputs the predicted 2D slices. The sinogram generator generates a generated sinogram that may be randomly generated or selected from training sinograms. The CNN inputs the generated sinogram and outputs predicted 2D slices of a 3D image based on the generated sinogram. The 1D encoder has weights that are adjusted during training. The discriminator inputs the predicted 2D slices and inputs training 2D slices from the training data store and generates an indication (e.g., probability) as to whether the predicted 2D slices represents a real sinogram based on the assumption that the training 2D slices are real 2D slices that represent real sinograms. The loss function generates a loss value to guide the adjusting of the weights of the 1D encoder and the discriminator. The 1D encoder may be an attention-based 1D CNN that interprets a sinogram as sequence of views and outputs a latent that represents an encoding of the sinogram. The 2D generator may be a pre-trained, convolutional-transpose 2D CNN that inputs a latent vector and outputs predicted 2D slices of a 3D image by the sinogram. The initializing of the initial 2D slices for the reconstruction algorithm to the predicted 2D slices allows for both faster convergence to a solution and a more accurate solution than, for example, standard initialization techniques that, for example, set the initial 2D slices for the reconstruction algorithm to all zeros. Although the CNN is described as being trained using an adversarial approach, other techniques may be used to train the CNN such as supervised learning that employs training data that includes training sinograms and corresponding training 2D slices. When the CNN IR system is employed to predict a 3D image, the sinogram encoder would be a 2D encoder and the image decoder would be a 3D encoder.

In some embodiments, the CNN IR system may employ a loss function that factors a mean square error (mse) loss, an adversarial (adv) loss, a structural similarity index measure (ssim) loss, and forward projection (fp) loss. The forward projection loss is based on differences between the sinogram generated by the sinogram generator and a predicted sinogram from the predicted 2D slices. The loss function may be represented by the following equation:

$$L = \alpha L_{mse} + (1-\alpha) L_{ssim} + \beta L_{adv} + \gamma L_{fp}$$

where $L_{mse}$ is a mean square error loss, $L_{ssim}$ is a structural similarity index measure loss, $L_{adv}$ is an adversarial loss, $L_{fp}$ is a forward projection loss, and $\alpha$, $\beta$, and $\gamma$ are weights for the losses. The forward projection loss is used to minimize the difference between the generated sinogram and the forward projected sinogram (i.e., predicted sinogram) generated from the predicted image. The structural similarity index measure loss may the loss described in Z. Wang, A. C. Bovik, H. R. Sheikh, and E. P. Simonelli, "Image Quality Assessment: From Error Visibility to Structural Similarity," IEEE Trans. Image Proc., 13(4):600-612, 2004, which is hereby incorporated by reference.

The CNNIR system uses the CNN to generate initial 2D slices for the reconstruction algorithm to provide perceptual features derived from the training 2D slices to effectively suppress noise and local changes in pixels of the predicted 2D slices. This initialization helps ensure that the final 2D slices (i.e., reconstructed 2D slices) are not inconsistent with the sinogram. To help minimize the inconsistencies, the CNNIR system employs the forward projection loss. The forward projection loss may be represented by the following equation:

$$L_{fp} = \|X - FP((\hat{Y})^*)\|_2^2$$

where X represent the generated sinogram, $\hat{Y}$ and predicted 2D slices, P(•) represents a forward projection operation, and * denotes a subset of the predicted sinogram that corresponds to the generated sinogram.

The CNNIR system may employ a SSIM loss as described in Z. Wang, A. C. Bovik, H. R. Sheikh, and E. P. Simonelli, "Image Quality Assessment: From Error Visibility to Structural Similarity," IEEE Trans. Imag. Proc., 13(4):600-612, 2004, which is hereby incorporated by reference.

Figure 2:
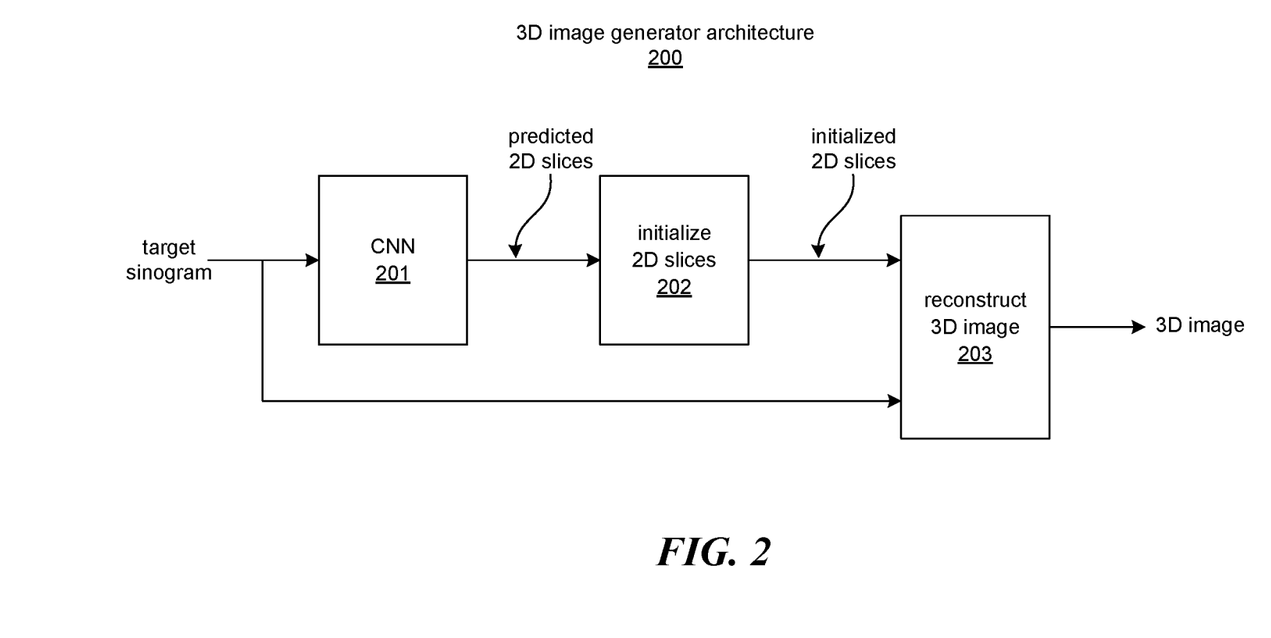
FIG. 2 is a block diagram that illustrates a 3D image generator architecture in some embodiments.

FIG. 2 is a block diagram that illustrates a 3D image generator architecture in some embodiments. The 3D image generator architecture 200 includes a CNN 201, an initialize 2D slices component 202, and a reconstruct 3D image component 203. The CNN, which may be training using the architecture of FIG. 1, inputs a target sinogram and outputs predicted 2D slices. The initialize 2D slices component inputs the predicted 2D slices and initializes the 2D slices for the reconstruction algorithm. The reconstruction 3D image component inputs the initialized 2D slices and the target sinogram and reconstructs a 3D image representing the target volume from which the target sinogram was collected.

The CNN IR system may employ a modified version of a CT-net that is adapted for few-view CT applications and that generates a 3D image from a sinogram. A CT-net is described in R. Anirudh, H. Kim, J. J. Thiagarajan, K. A. Mohan, K. Champley, and T. Bremer, "Lose the views: Limited Angle CT Reconstruction via Implicit Sinogram Completion," 2018 IEEE Conference on Computer Vision and Pattern Recognition, pp. 6343-6350, 2018, which is hereby incorporated by reference. Unlike limited-view reconstruction, however, the sinograms in few-view CT is spatially less coherent and the number of projections is smaller compared to reconstruction limited views. To compensate for the smaller number of views, the CNNIR system may employ filter sizes in the 1D CNN that are smaller than those employed by limited-view CT. The CNNIR system may also employ residual blocks to capture different levels of features from the sinogram and to help avoid overfitting. (See, K. He, X. Zhang, S. Ren and J. Sun, "Deep Residual Learning for Image Recognition," 2016 *IEEE Conference on Computer Vision and Pattern Recognition (CVPR)*, Las Vegas, Nev., 2016, pp. 770-778, which is hereby incorporated by reference.)

In some embodiments, the CNNIR system may employ a Regularized Least Squares (RLS)-based iterative algorithm to reconstruct the 2D slices of the 3D image. The CNNIR employs the RLS algorithm to reconstruct the 3D image based on the following optimization equation:

$$\hat{X} = \operatorname*{argmin}_{x} \|y - Ax\|^2 + \beta R(x) \quad (1)$$

where y is measured sinogram data, $\hat{X}$ is the reconstructed linear attenuation coefficients of the target volume, A is an X-ray projection matrix subject to the projection geometry, and R(x) is a Total Variation regularization functional, and β is a weight to that controls the strength of the regularization. The β term is determined empirically.

The computing systems on which the CNNIR system may be implemented may include a central processing unit, input devices, output devices (e.g., display devices and speakers), storage devices (e.g., memory and disk drives), network interfaces, graphics processing units, accelerometers, cellular radio link interfaces, global positioning system devices, and so on. The computing systems may include servers of a data center, massively parallel systems, and so on. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the CNNIR system. The data transmission media are used for transmitting data via transitory, propagating signals or carrier waves (e.g., electromagnetism) via a wired or wireless connection. The CNNIR system may be described in the general context of computer-executable instructions, such as program modules and components, executed by one or more computers, processors, or other devices. Generally, program modules or components include routines, programs, objects, data structures, and so on that perform particular tasks or implement particular data types. Typically, the functionality of the program modules may be combined or distributed as desired in various embodiments. Aspects of the CNN IR system may be implemented in hardware using, for example, an application-specific integrated circuit (ASIC).

Figure 3:
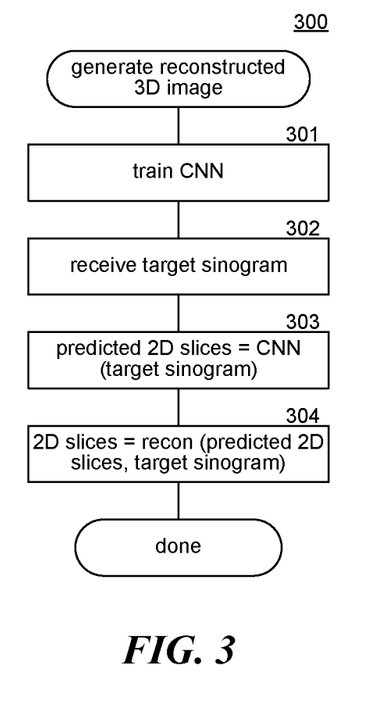
FIG. 3 is a block diagram that illustrates the processing of 3D image component of a CNNIR system in some embodiments.

FIG. 3 is a block diagram that illustrates the processing of 3D image component of a CNNIR system in some embodiments. The 3D image component 300 employees to a trained CNN to generate from a target sinogram of a target volume predicted 2D slices of a 3D image the represents the target volume. In block 301, the component employs a GAN to train the CNN based on training 2D slices. In block 302, the component receives a target sinogram of a target volume whose 3D image is to be reconstructed. In block 303, the component inputs a target sinogram and employs the CNN to generate predicted 2D slices. In block 304, the component inputs the predicted 2D slices and target sinogram and employs a reconstruction algorithm to generate 2D slices of a 3D image of the target volume.

Figure 4:
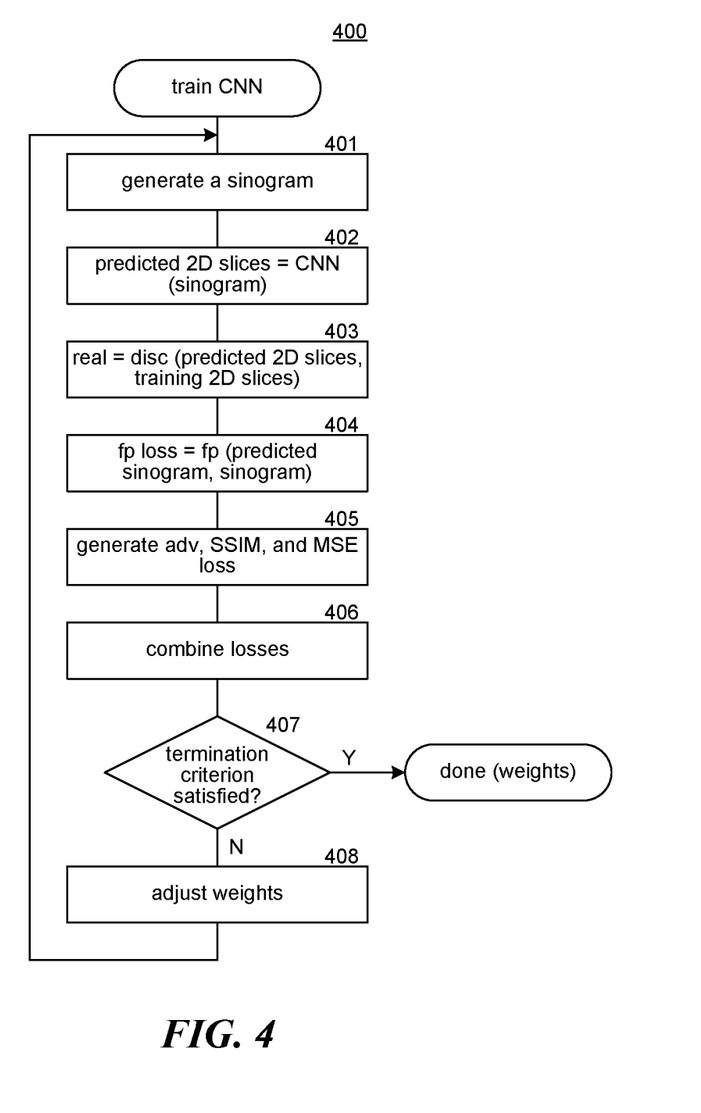
FIG. 4 illustrates the processing of a train CNN component of the CNNIR system in some embodiments.

FIG. 4 illustrates the processing of a train CNN component of the CNNIR system in some embodiments. The train CNN components 400 inputs training 2D slices used in training the CNN. The component loops until a termination criterion is satisfied based on the value of the loss function. In block 401, the component generates a sinogram. In block 402, the component employs a CNN to generate predicted 2D slices of the 3D image that represent the generated sinogram. In block 403, the component employs a discriminator to generate an indication of whether the generated sinogram is real based on the training 2D slices and the predicted 2D slices. The component also generates a predicted sinogram by forward projecting the predicted 2D slices. In block 404, the component calculates a forward projection loss based on the generated sinogram and a predicted 2D sinogram that is a forward projection of the predicted 2D slices. In block 405, the component generates an adversarial, structural similarity index measure, and mean squared error loss. In block 406 the component combines the losses. In decision block 407, if the combined loss satisfies a termination criterion (e.g., less than a loss threshold), then the component completes providing the weights for the 1D encoder and the discriminator, else the component continues at block 408. In block 408, the component adjusts the weights and loops to block 401 to generate a sinogram for the next iteration. The component may use a gradient descent technique when adjusting the weights.

A CNN is a type of neural network that has been developed specifically to process images. A CNN has multiple layers such as a convolutional layer, a rectified linear unit ("ReLU") layer, a pooling layer, a fully connected ("FC") layer, and so on. Some more complex CNNs may have multiple convolutional layers, ReLU layers, pooling layers, and FC layers.

A convolutional layer may include multiple filters (also referred to as kernels or activation functions). A filter inputs a convolutional window of an image, applies weights to each pixel of the convolutional window, and outputs an activation value for that convolutional window. For example, if the image is 256 by 256 pixels, the convolutional window may be 8 by 8 pixels. The filter may apply a different weight to each of the 64 pixels in a convolutional window to generate the activation value also referred to as a feature value. The convolutional layer may include, for each filter, a node (also referred to a neuron) for each pixel of the image assuming a stride of one with appropriate padding. Each node outputs a feature value based on a set of weights for the filter that are learned during a training phase for that node. Continuing with the example, the convolutional layer may have 65,536 nodes (256*256) for each filter. The feature values generated by the nodes for a filter may be considered to form a convolutional feature map with a height and width of 256. If an assumption is made that the feature value calculated for a convolutional window at one location to identify a feature or characteristic (e.g., edge) would be useful to identify that feature at a different location, then all the nodes for a filter can share the same set of weights. With the sharing of weights, both the training time and the storage requirements can be significantly reduced. If each pixel of an image is represented by multiple colors, then the convolutional layer may include another dimension to represent each separate color. Also, if the image is a 3D image, the convolution layer may include yet another dimension for each image within the 3D image. In such a case, a filter may input a 3D convolution window.

The ReLU layer may have a node for each node of the convolutional layer that generates a feature value. The generated feature values form a ReLU feature map. The ReLU layer applies a filter to each feature value of a convolutional feature map to generate feature values for a ReLU feature map. For example, a filter such as max (0, activation value) may be used to ensure that the feature values of the ReLU feature map are not negative.

The pooling layer may be used to reduce the size of the ReLU feature map by downsampling the ReLU feature map to form a pooling feature map. The pooling layer includes a pooling function that inputs a group of feature values of the ReLU feature map and outputs a feature value. For example, the pooling function may generate a feature value that is an average of groups of 2 by 2 feature values of the ReLU feature map. Continuing with the example above, the pooling layer may have 128 by 128 pooling feature map for each filter.

The FC layer includes some number of nodes that are each connected to every feature value of the pooling feature maps. For example, if an image is to be classified as being a cat, dog, bird, mouse, or ferret, then the FC layer may include five nodes whose feature values provide scores indicating the likelihood that an image contains one of the animals. Each node has a filter with its own set of weights that are adapted to the type of the animal that the filter is to detect. The CNN IR system may employ a node for each pixel of the 2D slices.

GANs have been used in applications such as super resolution, image editing, and image-to-image translation. GANs parameterize complex, high-dimensional, non-linear image manifolds. The accurate parameterization of an image manifold provides a powerful regularization ("GAN prior") for a range of problems such as defense against adversarial attacks, anomaly detection, and compressive sensing. Despite the variabilities in their goals and formulations of these applications, an overarching requirement of these applications is the ability to project an observed image onto the image manifold at test time (e.g., after training).

The projecting of an image onto an image manifold involves an encoding step to represent the image as a latent vector in the latent space of a generator, followed by a decoding step to obtain the image from the image manifold given the latent vector. The decoding is typically carried out using a pre-trained generator model (e.g., convolutional neural networks ("CNNs")). The encoding step is typically implemented using two distinct family of approaches: (1) projected gradient descent ("PGD") and (2) a GAN coupled with an explicit encoder. The PGD approach is a latent space optimization strategy that minimizes the discrepancy between an observed image and the best estimate of that observed image from the generator. A GAN coupled with an explicit encoder includes an additional network that explicitly provides a latent space representation for an image. Other approaches may employ different generative modeling techniques such as variational autoencoders (VAEs).

The following paragraphs describe various embodiments of aspects of the CNNIR system. An implementation of the CNNIR system may employ any combination of the embodiments. The processing described below may be performed by a computing device with a processor that executes computer-executable instructions stored on a computer-readable storage medium that implements the CNNIR system.

In some embodiments, a method performed by one or more computing systems is provided for generating a 3D representation of a 3D image of a target volume from target views representing a scan of the target volume. The method generates an initial 3D representation by inputting the target views to a convolutional neural network (CNN) that is trained to generate a 3D representation from target views. The method reconstructs the 3D representation from the target views and the initial 3D representation. In some embodiments, the target views are electromagnetic views of electromagnetic signals transmitted by an electromagnetic transmitter and collected by an electromagnetic collector. In some embodiments, the 3D representation is a 3D image and the CNN includes a 2D decoder that inputs target views and outputs a latent encoding, and a 3D encoder that inputs a latent encoding and outputs a 3D image. In some embodiments, the 3D representation includes 2D slices of a 3D image and the CNN includes a 1D decoder that inputs target views and outputs a latent encoding and a 2D encoder that inputs a latent encoding an outputs 2D slices of a 3D image. In some embodiments, the training data for the training includes training views and the training generates using an encoder and a decoder of the CNN to generate predicted 3D representations of predicted 3D images from the training views, generates predicted views from the predicted 3D representations, generates using a discriminator an indication of whether the predicted 3D representations are real, and adjusts weights of the encoder and the discriminator factoring in the indication and a comparison of the generated collection and the predicted collection. In some embodiments, training data for the training includes training views. The training generates using an encoder and a decoder of the CNN to generate predicted 3D representations of predicted 3Ds image from the training views, generates predicted views from the predicted 3D representations, generates using a discriminator an indication of whether the predicted 3D representations are real, and adjusts weights of the encoder and the discriminator factoring in the indication and a structural similarity index measure. In some embodiments, the collected views are X-ray views are collected by a computed tomography scanner, and the CNN is trained using an adversarial approach.

In some embodiments, a method performed by one or more computing system is provided for generating 2D slices of a 3D image of a target volume. The method receives a target sinogram collected during a computed tomography scan of the target volume. Each target view of the target sinogram is collected by an X-ray detector that detects X-rays transmitted by an X-ray scanner through the target volume. Each target view is associated with an angle from which the target view was collected. The method inputs the target sinogram to a convolutional neural network (CNN) to generate predicted 2D slices of the 3D image. The CNN is trained using training 2D slices of training 3D images. The method initializes 2D slices to the predicted 2D slices. The method reconstructs final 2D slices of the 3D image from the target sinogram and the initialized 2D slices. In some embodiments, the CNN is trained using a loss function that inputs a value output from a discriminator. In some embodiments, the training generates a predicted sinogram from predicted 2D slices and factors in difference between predicted sinogram and a generated sinogram from which the predicted 2D slices were generated. In some embodiments, the training factors in a structural similarity index measure reflecting differences between the predicted 2D slices and the training 2D slices. In some embodiments, the reconstructing applies a regularized least squared iterative algorithm.

In some embodiments, one or more computing systems are provided that generates a 3D image of a target volume from a target sinogram of target views collected during a scan of the target volume. The or more computing systems comprise one or more computer-readable storage mediums for storing computer-executable instructions and one or more processors for executing the computer-executable instructions stored in the one or more computer-readable storage mediums. The instructions input target sinogram, generate a predicted 3D image by inputting the target sinogram to a convolutional neural network (CNN) to generate the predicted 3D image, initialize the 3D image to the predicted 3D image, reconstruct a final 3D image from the target sinogram and the initialized 3D image, and output the final 3D image as the 3D image. In some embodiments, the target views are electromagnetic views of electromagnetic signals transmitted by an electromagnetic transmitter and collected by an electromagnetic collector. In some embodiments, the target sinogram is a few-view sinogram. In some embodiments, the CNN includes a 2D decoder that inputs a target sinogram and outputs a latent encoding and a 3D encoder that inputs a latent encoding and outputs a 3D image. In some embodiments, the CNN is trained using training data that includes training sinograms of training 3D objects and wherein the training generates predicted 3D images, generates predicted sinograms from the predicted 3D images, and factors in difference between the predicted sinograms and the training sinograms. In some embodiments, the training factors in an indication as to whether a predicted 3D image is real. In some embodiments, the sinograms are X-ray views collected by a computed tomography scanner. In some embodiments, the one or more computing systems further comprise one or more devices that collect the target sinogram, that send the target sinogram to a computing system to have the 3D image generated, and that receives the final 3D image that is output.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. Accordingly, the invention is not limited except as by the appended claims.

We claim:

1. A method performed by one or more computing systems for generating a 3D representation of a 3D image of a target volume from target views representing a scan of the target volume, the method comprising:
   generating an initial 3D representation by inputting a plurality of unreconstructed target views representing the scan of the target volume to a convolutional neural network (CNN) that is trained to generate a 3D representation from unreconstructed target views; and
   reconstructing the 3D representation from the plurality of unreconstructed target views and the initial 3D representation.

2. The method of claim 1 wherein the plurality of unreconstructed target views are electromagnetic views of electromagnetic signals transmitted by an electromagnetic transmitter and collected by an electromagnetic collector.

3. The method of claim 1 wherein the 3D representation is a 3D image and the CNN includes: a 2D decoder that inputs target views and outputs a latent encoding, and a 3D encoder that inputs the latent encoding and outputs a 3D image.

4. The method of claim 1 wherein the 3D representation includes 2D slices of a 3D image and the CNN includes a 1D decoder that inputs unreconstructed target views and outputs a latent encoding and a 2D encoder that inputs the latent encoding an outputs 2D slices of a 3D image.

5. The method of claim 1 wherein training data for a training of the CNN includes training views, wherein the training:
   generates using an encoder and a decoder of the CNN predicted 3D representations of predicted 3D images from the training views;
   generates predicted views from the predicted 3D representations;
   generates using a discriminator an indication of whether the predicted 3D representations are real; and
   adjusts weights of the encoder and the discriminator factoring in the indication and a comparison of a training collection and the predicted 3D representations.

6. The method of claim 1 wherein training data for a training of the CNN includes training views, wherein the training:
   generates using an encoder and a decoder of the CNN predicted 3D representations of predicted 3Ds image from the training views;
   generates predicted views from the predicted 3D representations;
   generates using a discriminator an indication of whether the predicted 3D representations are real; and
   adjusts weights of the encoder and the discriminator factoring in the indication and a structural similarity index measure.

7. The method of claim 1 wherein the collected views are X-ray views are collected by a computed tomography scanner and wherein the CNN is trained using an adversarial approach.

8. One or more computing systems that generates a resulting 3D image of a target volume from a target sinogram including a plurality of unreconstructed target views collected during a scan of the target volume, one or more computing system comprising: one or more non-transitory computer-readable storage mediums for storing computer-executable instructions for controlling the one or more computing systems to: input the target sinogram including the plurality of unreconstructed target views; generate a predicted 3D image by inputting the target sinogram including the plurality of unreconstructed target views to a convolutional neural network (CNN) to generate the predicted 3D image; initialize the 3D image to the predicted 3D image; reconstruct a final 3D image from the target sinogram including the plurality of unreconstructed target views and the initialized 3D image; and output the final 3D image as the resulting 3D image; and one or more processors for executing the computer-executable instructions stored in the one or more non-transitory computer-readable storage mediums.

9. The one or more computing systems of claim 8 wherein the plurality of unreconstructed target views are electromagnetic views of electromagnetic signals transmitted by an electromagnetic transmitter and collected by an electromagnetic collector.

10. The one or more computing systems of claim 8 wherein the target sinogram is a few-view sinogram.

11. The one or more computing systems of claim 8 wherein the CNN includes a 2D decoder that inputs a target sinogram and outputs a latent encoding and a 3D encoder that inputs the latent encoding and outputs a 3D image.

12. The one or more computing systems of claim 11 wherein the CNN is trained using training data that includes training sinograms of training 3D objects and wherein the training generates predicted 3D images, generates predicted sinograms from the predicted 3D images, and factors in difference between the predicted sinograms and the training sinograms.

13. The one or more computing systems of claim 11 wherein the training factors in an indication as to whether a predicted 3D image is real.

14. The one or more computing systems of claim 8 wherein the sinograms are X-ray views collected by a computed tomography scanner.

15. The one or more computing systems of claim 8 further comprising one or more devices that collect the target sinogram, that send the target sinogram to a computing system to have the 3D image generated, and that receive the final 3D image that is output.

* * * * *